United States Patent
Schlenk et al.

(10) Patent No.: US 9,820,817 B2
(45) Date of Patent: Nov. 21, 2017

(54) ROBOT SYSTEM

(71) Applicant: Deutsches Zentrum Fur Luft-und Raumfahrt E.V., Cologne (DE)

(72) Inventors: Christopher Schlenk, Munich (DE); Ulrich Hagn, Munich (DE); Jan Koenig, Munich (DE)

(73) Assignee: DEUTSCHES ZENTRUM FUER LUFT-UND RAUMFAHRT E.V., Cologne (DE)

( * ) Notice: Subject to any disclaimer, the term of this patent is extended or adjusted under 35 U.S.C. 154(b) by 90 days.

(21) Appl. No.: 14/668,121

(22) Filed: Mar. 25, 2015

(65) Prior Publication Data

US 2015/0272685 A1   Oct. 1, 2015

(30) Foreign Application Priority Data

Mar. 25, 2014   (DE) ........................ 10 2014 004 238

(51) Int. Cl.
  *A61B 19/00* (2006.01)
  *A61B 90/50* (2016.01)
  *A61B 34/30* (2016.01)

(52) U.S. Cl.
  CPC .......... *A61B 19/2203* (2013.01); *A61B 34/30* (2016.02); *A61B 90/50* (2016.02)

(58) Field of Classification Search
  CPC ..... A61B 19/2203; A61B 34/30; A61B 90/50; A61B 90/361; A61B 1/00149; A61B 1/04; A61B 2090/064; G05B 15/02; G05B 2219/39327; G05B 2219/40613; G05B 2219/41397
  USPC .................................. 248/694, 129; 700/245
  See application file for complete search history.

(56) References Cited

U.S. PATENT DOCUMENTS

| | | | |
|---|---|---|---|
| 5,553,198 A | 9/1996 | Wang et al. | |
| 8,313,070 B2 | 11/2012 | Kronner et al. | |
| 9,089,352 B2 * | 7/2015 | Jeong ................. | A61B 19/2203 |
| 2006/0142657 A1 * | 6/2006 | Quaid .................... | A61N 1/372 |
| | | | 600/424 |
| 2015/0032164 A1 * | 1/2015 | Crawford ........... | A61B 19/2203 |
| | | | 606/279 |
| 2015/0250547 A1 * | 9/2015 | Fukushima ............ | G05B 15/02 |
| | | | 606/130 |

FOREIGN PATENT DOCUMENTS

| | | |
|---|---|---|
| DE | 69112538 T2 | 3/1996 |
| DE | 102006012766 A1 | 9/2007 |

OTHER PUBLICATIONS

Examination Report dated Dec. 8, 2014 for priority German application No. 102014004238.3.

* cited by examiner

*Primary Examiner* — Anita M King
(74) *Attorney, Agent, or Firm* — Ohlandt, Greeley, Ruggiero & Ruggiero, LLP

(57) ABSTRACT

A robot system is provided that includes a transport device and a robot. The transport device has a receiving device that receives a robot and a movement device connected with the receiving device. The robot has a robot base with at least one manipulator element connected with the robot base. The robot system further includes a fastening device connected with the robot base for fastening the robot to a holding device and includes a transport device receiver that is connected with the robot base for fastening the robot to the transport device.

31 Claims, 2 Drawing Sheets ness of a universally useable fastening
ROBOT SYSTEM

CROSS REFERENCE TO RELATED APPLICATIONS

The present invention claims the priority of German Patent Application no. DE 10 2014 004 238.3 filed on Mar. 25, 2014, the disclosure of which IS incorporated herein by reference.

BACKGROUND OF THE INVENTION

Field of the Invention

The invention relates to a robot system with a transport device and a robot.

Description of the Prior Art

Surgical robots have become firmly established in various fields of surgery. Among others, the possible applications of surgical robots include placing pedicle screws, navigated biopsies in the field of neurosurgery, as well as endoscopic telesurgery.

In order to be able to respond to the ever changing tasks and possible applications in robotic surgery, robot systems have to be of a flexible design.

Typical robot systems fixedly installed in an operating theatre (OR) are thereby considerably limited in their flexibility. The space required for fixedly installed robot systems is not available in the often constricted ORs even if the robot system is not in use. Thereby, the operating theatre staff is unnecessarily hindered in performing its work. At the same time, in this case, the robot system cannot be used for another purpose for the duration of the surgery. In particular, the fixedly installed robot system cannot be used for another operation. Further, retrofitting an existing OR with fixedly installed robot systems causes considerable reconstruction costs. Moreover, during maintenance work on a fixedly installed robot system, the corresponding OR cannot be used, whereby the number of operations that can be carried out there is lowered and thereby a hospital's profit is reduced. In addition, with fixedly installed robot systems, the range of a robot arm of the robot system is defined, so that the accessibility of a surgical area by the robot cannot be changed afterwards. This restriction in accessibility can be counteracted by providing a rail system along which the robot is displaceably mounted. However, retrofitting the rail system in existing ORs requires considerable effort and costs.

On the other hand, the bases of the robots have to be fixed securely during an operation, so as to achieve the required precision during the surgical procedures and to exclude any risk to the patient. In this regard, the fixation has to be capable not only to bear the weight, but also to absorb all forces and moments of the moving robot and to keep its position and orientation as exactly as possible during the process. This results in high requirements on the fastening of the robot.

It is particularly preferred to fasten the robot system to the surgical table, since relative movements between the robot base and the surgical table can thereby be avoided, the robots are close to the surgical area and every change in the vertical adjustment or the inclination of the surgical table is automatically carried out in line. A robot system connected with a rail system of a surgical table is known from U.S. Pat. No. 5,553,198, for example. Feasibly, the existing surgical tables are still used so that a hospital can save the costs of a modification or even the acquisition of new surgical tables. A suitable fastening element, either provided as a standard feature of almost all surgical tables or can be retrofitted, is represented by the lateral rails of surgical tables, standardized according to DIN EN ISO 19054. Their specific design and their mechanical strength are defined by the standard, whereby the construction of a universally useable fastening mechanism is drastically simplified.

A fastening to rail systems, in particular to existing rail systems, is cumbersome with common robot systems, since they require in particular a manual fixation for which the robot must first be carried to the rail by the operation theatre staff and must then be connected to the rail. Such a robot system is known for example from U.S. Pat. No. 8,313,070. In many instances, fastening to the rail system, in particular an existing rail system, requires a tool and is further hindered by the robot system's sterile plastic cover necessary during surgery. Further, manual fastening bears the risk of dropping the robot or of the robot falling due to an incorrect fastening. This could lead to substantial damage to the robot, or the patient and the operation theatre staff could be hurt, respectively.

SUMMARY OF THE INVENTION

It is an object of the invention to provide a robot system for a simplified provision and a secure fastening at the place of use.

The object is achieved with a robot system as defined herein, with a transport device as defined herein, as well as a robot and methods as defined herein.

The transport device of the present invention, in particular for surgical robots, comprises a receiving means for receiving a robot, in particular a portable robot. A movement device is connected with the receiving means. Owing to the movement device, the receiving means is movable and can thus be moved to a respective place of use. In particular, the movement device is in the form of rollers or a hover cushion. Specifically, if the movement device is in the form of rollers, it is preferred that at least two rollers are provided with suitable roller brakes. In particular, providing all rollers with suitable roller brakes facilitates the fixation of the movement device at the place of use, if access to some rollers is difficult (e.g. because of other apparatus, the surgical table etc.).

In particular, the robot may comprise more than one robot arm which arms are preferably connected with each other via a common robot basis.

Preferably, the transport device comprises a plurality of receiving means so that a plurality of robots, in particular portable robots, can be transported on one transport device.

In particular, the height of at least one receiving means is variable. Thereby, the height of the receiving means may be adjusted to the position of a robot so as to receive the robot in the receiving means. Specifically, the height can be adjusted by means of a mechanic, electric, hydraulic or pneumatic drive, where a mechanical drive, for example, is provided with a crank handle. Preferably, the height of all receiving means can be adjusted together, whereby the design of the transport device is simplified.

In particular, the receiving means is movable in a horizontal plane by means of the movement device. Thereby, the receiving means can be moved to the robot to receive the same. Especially, if a height adjustment of the receiving means is provided, the receiving means can thus be moved to the robot.

In particular, the receiving means is provided with a (transport device) locking device for locking the robot in the receiving means. Thereby, an unintentional disengagement of the robot from the receiving means is prevented. For this purpose, the locking device preferably comprises a locking element pre-tensioned towards a closed position. In this manner, an unintentional opening of the locking device is also prevented. The locking element has to be moved actively from the locked position to an open position to release the robot. The pre-tensioning of the locking element may be generated by a spring mechanism, for example.

Specifically, the receiving means comprises positioners for a precise positioning of the robot in the receiving means. The positioners may be positioning screws and/or contact edges. In particular, the positioners serve to ensure that the robot is connected with the receiving means such that the locking element can be moved into the closed position.

The robot of the present invention, which in particular is a surgical robot, comprises a robot base and at least one robot arm connected with the robot base. Further, a fastening device is connected with the robot base for fastening the robot to a holding device. The robot basis is also connected with a transport device receiving means for connecting the robot with a transport device.

The holding device may be a rail system, for example, and preferably is a lateral rail of a surgical table as defined in standard DIN EN ISO 19054. However, other rail systems are conceivable, while a lateral rail as defined in standard DIN EN ISO 19054 exists at most surgical tables or could be retrofitted to the same. Thereby, when compared with alternative solutions, costs for otherwise necessary reconstruction measures are avoided.

In particular, the fastening device at the same time is the transport device receiving means. Thereby, the fastening device can be used to fasten the robot to a holding device, while the robot can also be fastened to a transport device via the fastening device, which acts as a transport device receiving means. However, it is preferred that the fastening device and the transport device receiving means are two separate components so that the robot can be simultaneously connected with a holding device and a transport device.

In particular, the fastening device is movable in a horizontal plane. Thereby, the fastening device can be moved to a holding device in order to connect the robot with a holding device.

In particular, the fastening device comprises at least one movable holding jaw and at least one stationary holding jaw. Preferably, the movable holding jaw is designed such that it can be moved towards the stationary holding jaw. With the fastening device open, the movable holding jaw and the stationary holding jaw are further apart than in the closed state of the fastening device. The robot is connected, in particular clampingly, with the holding device by closing the holding jaws, with the movable holding jaw being moved towards the stationary holding jaw. The robot is thus fixed to the holding device. A first connection of the robot with the holding device can be made by means of the stationary holding jaw, with no further positional change occurring during the closing of the fastening device. Preferably, the movable holding jaw is moved perpendicularly towards the stationary holding jaw. It is particularly preferred that this movement follows a vertical direction. A uniform fastening of the fastening device is achieved thereby.

Preferably, the at least one movable holding jaw is formed such that it surrounds the lower or upper part of the holding device. Correspondingly, the stationary holding jaw is designed such that it surrounds the upper or the lower part of the holding device. It is particularly preferred that the stationary holding jaw surrounds the upper part of the holding device so that the stationary holding jaw can first be connected with the holding device and can thereafter be fixed by means of the movable holding jaw.

In particular, the movable holding jaw and/or the stationary holding jaw have a bevel arranged on a side facing the holding device. This allows for a precise position of the robot on the holding device, since, in the event of an imprecise positioning of the robot, the same is moved to the predefined position by virtue of the bevels. In particular, the bevel is provided on a side of the fastening device averted from the robot. Thus, when closing the fastening device, the robot is moved towards the holding device by virtue of the bevels. Thereby, a secure and stable fastening of the robot to the holding device is achieved.

Specifically, the movable holding jaw is connected with a push rod clamping device or another quick closing means. Thereby, the fastening device can be closed in a quick and simple manner, in particular also if the robot is covered by a sterile plastic film as is typically the case during a surgical operation. Specifically, no tool is required and closing the fastening device requires no particular training of the staff, thus saving time and costs.

Preferably, the fastening device comprises at least two movable holding jaws, wherein at least one holding jaw is designed such that, in the closed position, it allows for a displacement of the robot along the holding device, especially when the holding device is a rail. Further, at least one movable holding jaw is configured so as to prevent, when in its closed position, a displacement of the robot along the holding device. Thus, for a displacement of the robot along the holding device, not all movable holding jaws have to be brought into an open position, which would bear the risk of the robot unintentionally detaching from the holding device. Rather, it is only necessary to move the movable holding jaw to an open position which prevents a displacement along the holding device. The at least one movable holding jaw that allows a displacement of the robot along the holding device when in its closed position, remains closed.

In particular, the fastening device is in surface contact with the holding device. The surface contact is caused specifically by a surface element. Forces and moments acting on the robot can thereby be transmitted better to the holding device.

In particular, the transport device receiving means comprises a (transport device) locking device for locking the connection of the robot with a transport device. The locking device prevents an unintentional disengagement of the robot from the transport device. Preferably, the locking device comprises a locking element pre-tensioned to a closed position, so that an unintentional opening of the locking device is prevented. Here, the pre-tensioning of the locking element may be generated by a spring mechanism, for example.

The robot system of the invention comprises a transport device and a robot as described above.

Specifically, the locking of the locking device can only be released if the fastening device is at least partly in a closed position. Especially, if the fastening device includes a plurality of movable holding jaws, releasing the locking of the locking device merely requires that at least one of the movable holding jaws is in a closed position, whereby the fastening device is at least partly in a closed position. As an alternative, it may also be necessary to move all movable holding jaws into the closed position in order to release the locking of the locking device. If, however, the fastening device only has one movable holding jaw, the locking of the locking device can only be released if this single holding jaw is in a closed position. Accordingly, when transferred from the transport device to the holding device or vice versa, the robot is always fixedly connected with the holding device, the transport device or both. The locking device is the transport device locking or the transport device receiving means locking.

In particular, the locking element comprises a contact surface against which the fastening device presses in the closed position, whereby the locking element is moved out of its closed position. The locking device is thereby moved into an open position by the closing of the fastening device, especially against pre-tensioning towards the closed position. A releasing of the locking element without a closing of the fastening device is hindered and, as is particularly preferred, prevented preferably by the pre-tensioning.

According to a development, the robot system comprises a guide system, wherein the transport device receiving means of the robot comprises a first guide element and the receiving means of the transport device comprises a second guide element, wherein the first guide element and the second guide element engage each other to connect the robot with the transport device. For this purpose, preferably, the first guide element or the second guide element comprises at least one bolt and the second guide element or the first guide element correspondingly comprises at least one recess into which the bolt engages when connecting the robot with the transport device. If, for example, the first guide element comprises a bolt, the second guide element is formed as a recess, with the number of bolts and the number of recesses provided matching. As an alternative, the first guide element may also comprise at least one bolt and at least one recess, with the second guide element correspondingly comprising at least one recess and at least one bolt, the bolt of the first guide element engaging the recess of the second guide element, and the bolt of the second guide element engaging the recess of the first guide element.

In particular, the first guide element is arranged at the fastening device and, as is particularly preferred, is arranged at the movable holding jaw.

Preferably, the first guide element and the second guide element are spaced from each other when the fastening device is in the closed position. As soon as the fastening device is moved into the closed position, the first and the guide element and the second guide element no longer engage each other and the transport device can be disengaged from the robot.

The invention further relates to a method for fastening a robot to a holding device, wherein the robot is fastened to a holding device by closing a fastening device, wherein a locking of the robot on a transport device is released by the closing of the fastening device. By releasing the locking, the robot is disengaged from the transport device. Thus disengaging the robot from transport device is possible only, if the robot is fixedly connected with the holding device by closing the fastening device.

In particular, prior to closing the fastening device, the height of the fastening device of the robot is adjusted to the holding device by means of the transport device. Thus, it is not necessary to adjust the height of the fastening device to the height of the holding device by manually lifting the robot.

The invention further relates to a method for detaching a robot from a holding device, wherein the robot is connected with a transport device, a fastening device is opened for the disengagement of the robot from the holding device, and the robot is locked to the transport device by opening the fastening device. Thereafter, the robot is disengaged from the holding device.

In particular, the fastening device can only be opened if the robot is positioned correctly in the receiving means. In this regard, it is particularly advantageous if the robot, when positioned correctly in the receiving means, the robot is arranged in the receiving means in a form-fitting manner. Preferably, the fastening device can only be opened if the robot has been fully connected with the transport device.

Preferably, the methods for fastening a robot to a holding device, as well as for detaching a robot from a holding device are developed in a manner corresponding to the robot system described above.

BRIEF DESCRIPTION OF THE DRAWINGS

A full and enabling disclosure of the present invention, enabling one of ordinary skill in the art to carry out the invention, is set forth in greater detail in the following description, including reference to the accompanying drawing in which.

DESCRIPTION OF PREFERRED EMBODIMENTS

Figure 1:
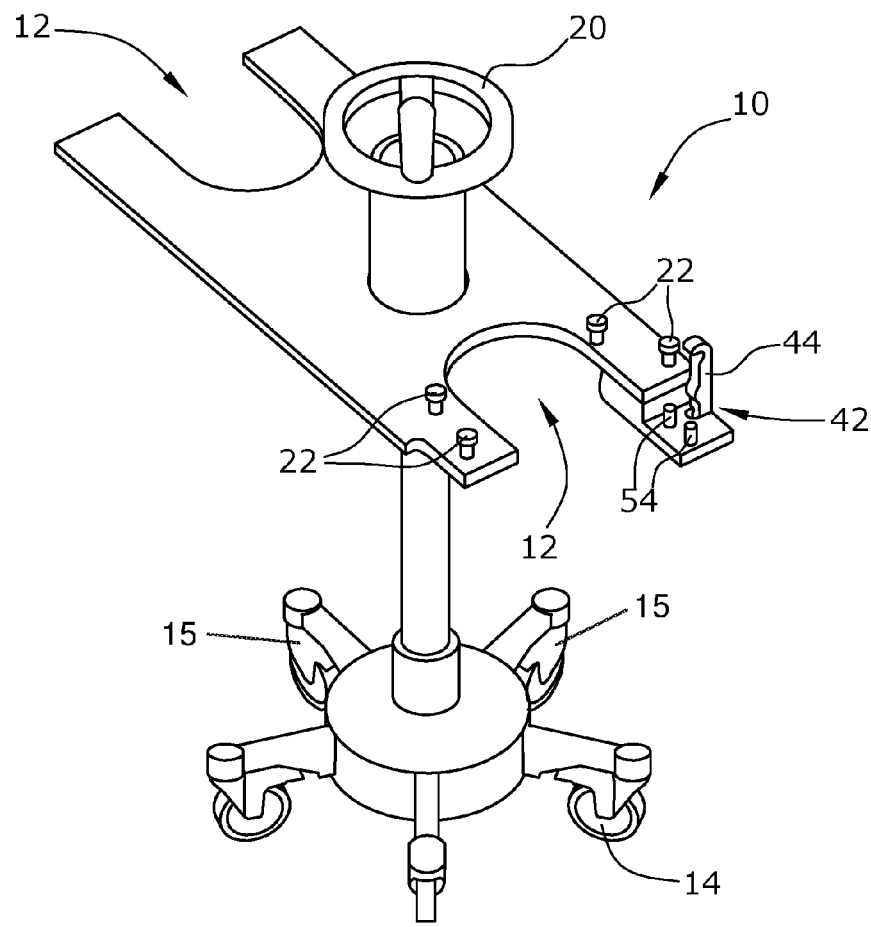
FIG. 1 illustrates a transport device according to the present invention.
Figure 2:
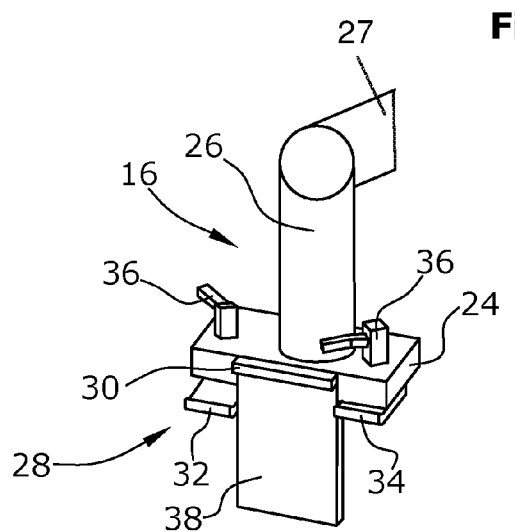
FIG. 2 illustrates a robot according to the present invention with a fastening device.

The drawing figures are intended to illustrate the general manner of construction and are not necessarily to scale. In the detailed description and in the drawing figures, specific illustrative examples are shown and herein described in detail. It should be understood, however, that the drawing figures and detailed description are not intended to limit the invention to the particular form disclosed, but are merely illustrative and intended to teach one of ordinary skill how to make and/or use the invention claimed herein.

FIG. 1 illustrates the transport device 10 of the present invention, comprising a receiving means 12 and a movement device with rollers 14. Owing to the rollers 14, the transport device 10 is freely movable and can therefore transport the robot 16 in a simple manner to the place of use. After the robot 16 is fastened to a holding device 18, the transport device 10 can be removed from the OR to save space. It is preferred that at least two rollers 14 are provided with suitable roller brakes 15. In particular, providing all rollers 14 with suitable roller brakes 15 facilitates the fixation of the movement device at the place of use, if access to some rollers 14 is difficult (e.g. because of other apparatus, the surgical table etc.).

Further, the transport device 10 comprises a height adjustment means operated by means of a hand wheel 20. By turning the hand wheel 20, the height of the receiving means 12 can be adapted to the holding device 18.

In order to ensure a more precise positioning of the robot 16 in the receiving means 12, the transport device 10 comprises positioners in the form of positioning screws 22. Preferably, these are shoulder screws. When all four positioning screws 22 contact the transport device receiving means 24, a correct positioning of the robot 16 in the receiving means 12 is guaranteed.

The robot 16 of the present invention comprises a robot basis or base 26 connected with at least one robot arm 27. A fastening device 28 is connected with the robot basis 26. The fastening device 28 comprises a stationary holding jaw 30, as well as a first movable holding jaw 32 and a second movable holding jaw 34. The first movable holding jaw 32 is illustrated in an open position, whereas the second movable holding jaw 34 is illustrated in a closed position. The movable holding jaws 32, 34 are preferably moved via push rod clamping devices 36 and are moved in particular perpendicularly towards the stationary holding jaw 30, so as to be able to be transferred from an open position to a closed position. Here, the first movable holding jaw 32 is designed such that, in its closed position, it prevents a displacement of the robot 16 along the holding device 18. In contrast thereto, the second movable holding jaw 34 is designed such that, in its closed position, it allows for the displacement of the robot 16 along the holding device 18. If, subsequently, the robot 16 is to be displaced to another position along the holding device 18, it is merely necessary to open the first movable holding jaw 32. The second movable holding jaw 34 remains in the closed position so that the robot 16 cannot be disengaged unintentionally from the holding device 18.

Further, the robot 16 comprises a surface element 38 by which a surface contact is made with the holding device.

Figure 3:
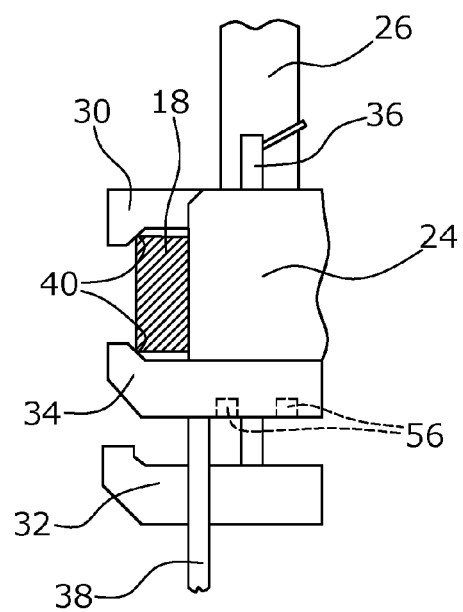
FIG. 3 is a detail of the fastening device of FIG. 2 in side elevational view.

Both the stationary holding jaw 30 and the movable holding jaws 32, 34 have bevels 40 (FIG. 3) provided on the side of the holding jaws 30, 32, 34 facing the holding device 18. In particular, the bevels 40 are provided on the side of the holding jaws 30, 32, 34 averted from the robot 16. Owing to the bevels 40, the robot 16 is moved towards the holding device 18 as the fastening device 28 is closed. Thus, it is possible to fix the robot 16 precisely at a predefined position relative to the holding device 18.

Figure 4:
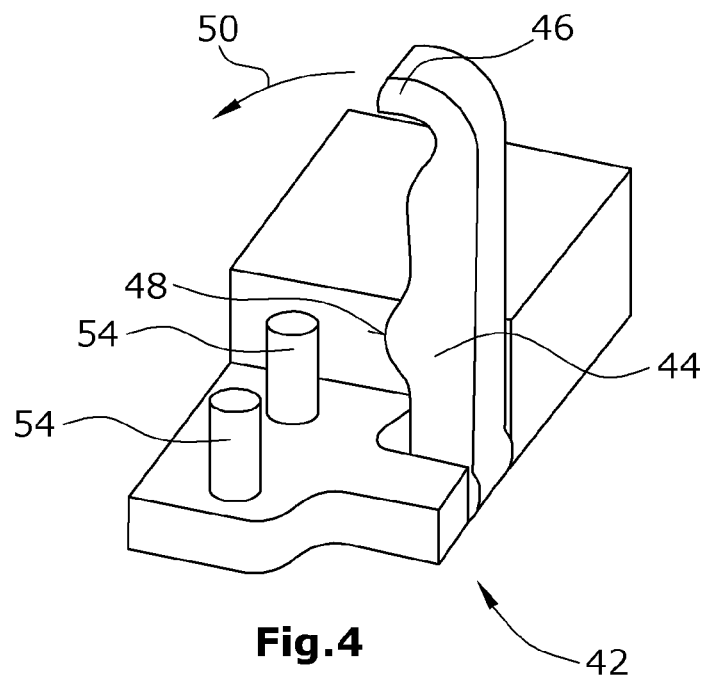
FIG. 4 is a detail of the transport device of FIG. 1 in perspective view.
Figure 5:
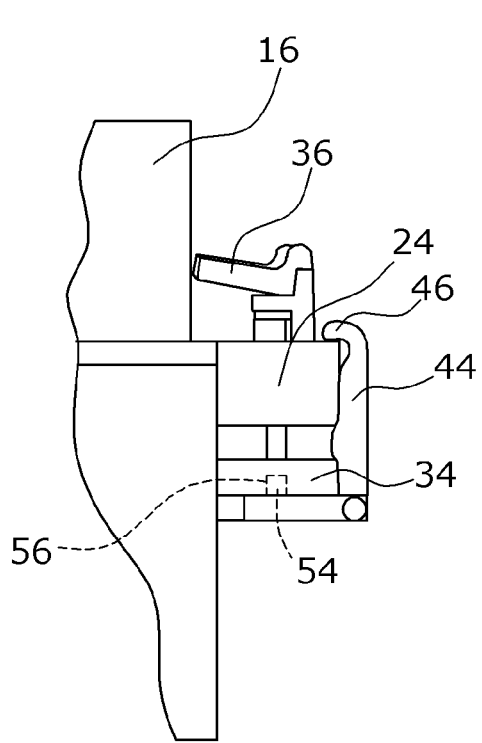
FIG. 5 is a detail of the robot of FIG. 2 in perspective view, with a fastening device in the open position.
Figure 6:
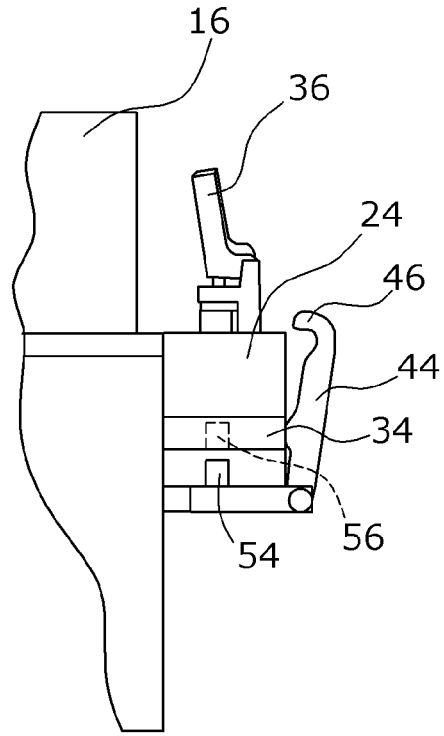
FIG. 6 is a detail of the robot of FIG. 2 with a fastening device in the closed position.

A locking device 42 is connected with the transport device 10, which comprises a locking element 44 (FIG. 4). The locking element 44 has a hook element 46 engaging into the transport device receiving means 24 or over its top surface. The locking element 44 has a contact surface 48 and is pre-tensioned in the direction of the arrow 50 by means of a spring (not illustrated). By this pre-tensioning, the locking element 44 is moved into a closed position. When the holding jaw 34 of the fastening device 28 is open, the robot 16 is not securely connected with the holding device 18. In order to prevent an unintentional disengagement of the robot 16 from the transport device 10, the locking element 44 locks the robot 16 in the transport device 10 by the hook element 46 engaging in the transport device receiving means 24 when the locking element 44 is in the closed position (FIG. 5). The robot 16 cannot be removed from the receiving means 12. The locking element 44 specifically prevents a vertical movement of the robot 16, while the bolts 54 prevent a horizontal movement of the robot. If the holding jaw 34 is moved to a closed position (FIG. 6), the holding jaw 34 presses against the contact surface 48 of the locking element 44. Thereby, the locking element 44 is moved from the closed position into an open position against the pre-tension of the spring. In the open position of the locking element 44, the hook element 46 no longer engages the transport device receiving means 24. With the holding jaw 34 closed, the robot 16 is securely connected with the holding device 18, and the robot 16 can be detached from the receiving means 12.

The receiving means 12 further comprises bolts 54 engaging into recesses 56 provided in at least one of the movable holding jaws 32, 34. The bolts 54 only engage into the recesses 56 if the movable holding jaw 34 is in an open position. As soon as the holding jaw 34 is moved into a closed position, the bolt 54 no longer engages into the recess 56 so that the robot 16 can be disengaged from the receiving means 12. The bolts 54 ensure that the holding jaw 34 can only be moved from a closed position into an open position if the robot 16 is positioned precisely in the receiving means 12. When the holding jaw 34 is moved into an open position, the bolts 54 engage the recesses 56, whereby the retaining jaw 34 is guided in its movement. If the holding jaw 34 is in an open position, the locking element 44 is moved in the direction of the arrow 50 by the pre-tension and the hook element 46 engages into the transport device receiving means 24. Thereby, the robot 16 is securely locked in the receiving means 12. A guiding of the robot 16 upward out from the receiving means 12 is thereby blocked.

Even if both the locking element in the embodiment illustrated cooperates with the second movable holding jaw 34 and the recesses are provided in the second movable holding jaw 34, it is possible as an alternative or in addition that the first movable holding jaw 32 cooperates with the locking element 44 and/or be provided with recesses 56 or bolts 54 of the guide system.

For connecting a robot 16 with a holding device 18, the transport device 10 is moved to the holding device 18 and, thereafter, the height of the receiving means 12 is adjusted to the holding device 18 by means of the rotary wheel 20.

First, the stationary holding jaw 30 is connected with the holding device 18. Thereby, the position of the robot is already substantially defined. Then, the movable holding jaws 32, 34 are moved into a closed position by means of the push rod clamping devices 36, whereby the robot 16 is clampingly fixed to the holding device. By closing the fastening device 28, the locking element 44 is moved out of its closed position, whereby the locking of the robot 16 in the transport device 10 is released. The transport device 10 can be disengaged from the robot 16 and the robot 16 is ready for use.

For a displacement of the robot 16 along the holding device 18, the holding jaw 32 is moved into the open position, the robot is displaced and the holding jaw 32 is moved back into the closed position. To detach the robot 16 from the holding device 18, the transport device 10 is moved to the robot 16, the height of the receiving means 12 being adjusted by means of the rotary wheel 20. Then, the robot 16 is positioned precisely in the receiving means 12 using the positioners. Thereafter, the fastening device 28 is moved into an open position by opening the push rod clamping devices 36, whereby the movable holding jaws 32, 34 are lowered. Due to the lowering, the bolts 54 engage into the recesses 56, whereby the robot 16 is secured against horizontal displacement relative to the transport device 10. As soon as the fastening device 28 is in an open position, the locking element 44 moves into a closed position, whereby the robot 16 is securely locked in the receiving means 12.

All references cited herein are incorporated by reference to the full extent to which the incorporation is not inconsistent with the express teachings herein.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

The invention claimed is:

1. A robot comprising
   a robot base,
   at least one robot arm connected with the robot base,
   a fastening device for fastening the robot to a holding device, the fastening device being connected with the robot base, and
   a transport device receiving means connecting the robot with a transport device, the transport device receiving means being connected with the robot base,
   wherein the transport device, comprises:
   a receiving means for receiving the robot, and
   a movement device connected with the receiving means.

2. The robot of claim 1, further comprising a plurality of receiving means.

3. The robot of claim 1, wherein the height of the receiving means is variable.

4. The robot of claim 2, wherein the receiving means comprises more than one receiving means and the height of all of the receiving means is jointly variable.

5. The robot of claim 1, wherein the receiving means can be moved in a horizontal plane by the movement device.

6. The robot of claim 1, further comprising a locking device for locking the robot in the receiving means, the locking device being connected with the receiving means.

7. The robot of claim 6, wherein the locking device comprises a locking element pre-tensioned towards a closed position.

8. The robot of claim 1, wherein the receiving means comprises positioners for a precise positioning of the robot in the receiving means.

9. The robot of claim 1, wherein the movement device comprises a plurality of rollers, at least two of said rollers comprising a brake device for fixing the movement device.

10. The robot of claim 1, wherein the fastening device is movable in a horizontal plane.

11. The robot of claim 1, wherein the fastening device comprises at least one movable holding jaw and at least one stationary holding jaw.

12. The robot of claim 11, wherein the movable holding jaw is movable in a vertical direction towards the stationary holding jaw, whereby the robot can be connected with the holding device in a clamping manner.

13. The robot of claim 11, wherein the movable holding jaw and/or the stationary holding jaw are provided with a bevel at a side facing the holding device at a side of the fastening device averted from the robot, so that the robot is moved towards the holding device by virtue of the bevel as the fastening device is closed.

14. The robot of claim 11, wherein the movable holding jaw is connected with a quick-acting clamp.

15. The robot of claim 1, wherein the fastening device has at least two movable holding jaws, wherein at least one movable holding jaw is configured to allow, when in its closed position, for a displacement of the robot along the holding device, and at least one movable holding jaw is configured to prevent, when in its closed position, a displacement of the robot along the holding device.

16. The robot of claim 1, wherein the fastening device is in surface contact with the holding device.

17. The robot of claim 1, wherein the transport device receiving means comprises a locking device for locking the connection of the robot with a transport device.

18. The robot of claim 17, wherein the locking device comprises a locking element pre-tensioned towards a closed position.

19. A robot system comprising
   the robot of claim 17, and
   a transport device comprising
   a receiving means for receiving the robot, and
   a movement device connected with the receiving means.

20. A robot system of claim 19, wherein the locking of the locking device can only be released if the fastening device is at least partly in a closed position.

21. The robot system of claim 19, wherein a locking element of the locking device comprises a contact surface against which the fastening device presses, when in its closed position, whereby the locking element is moved out of its closed position.

22. The robot system of claim 19, wherein a guide system, wherein the transport device receiving means of the robot comprises a first guide element and the receiving means of the transport device comprises a second guide element, wherein the first guide element and the second guide element engage each other to connect the robot with the transport device.

23. The robot system of claim 22, wherein the first guide element or the second guide element comprises at least one bolt, and the second guide element or the first guide element correspondingly comprises at least one recess into which the bolt engages when the robot is connected with the transport device.

24. The robot system of claim 22, wherein the first guide element is provided on the fastening device on the movable holding jaw.

25. The robot system of claim 22, wherein the first guide element and the second guide element are arranged spaced from each other when the fastening device is in its closed position so that the transport device and the robot can be disengaged.

26. A method for fastening a robot to a holding device, wherein in a first step the robot is fastened to the holding device by closing a fastening device, and in a second step a locking of the robot on a transport device is released by closing the fastening device, whereby in a third step the transport device is disengaged from the robot.

27. The method of claim 26, wherein, first, the height of the fastening device of the robot is adjusted to the holding device by the transport device.

28. The method of claim 26, wherein said method uses a robot system, comprising:
   (a) a robot comprising:
      a robot base;
      at least one robot arm connected with the robot base;
      a fastening device for fastening the robot to the holding device, the fastening device being connected with the robot base; and
      a transport device receiving means connecting the robot with the transport device, the transport device receiving means being connected with the robot base; and
   (b) a transport device, comprising:
      a receiving means for receiving the robot; and
      a movement device connected with the receiving means.

29. A method for disengaging a robot from a holding device, wherein
   in a first step
      the robot is connected with a transport device,
   in a second step a fastening device is opened to disengage the robot from the holding device, and the robot is locked on the transport device by opening the fastening device, and in a third step the robot is disengaged from the holding device.

30. The method of claim 29, wherein the transport device comprises a receiving means and the fastening device can be opened only if the robot is positioned correctly in a form-fitting manner, in the receiving means and is preferably fully connected with the transport device.

31. The method of claim 29, wherein said method uses a robot system, comprising:
(a) a robot comprising:
  a robot base;
  at least one robot arm connected with the robot base;
  a fastening device for fastening the robot to the holding device, the fastening device being connected with the robot base; and
  a transport device receiving means connecting the robot with the transport device, the transport device receiving means being connected with the robot base; and
(b) a transport device, comprising:
  a receiving means for receiving the robot; and
  a movement device connected with the receiving means.

* * * * *